(12) United States Patent
Norkin et al.

(10) Patent No.: US 8,956,671 B1
(45) Date of Patent: Feb. 17, 2015

(54) VOLATILE ORGANIC COMPOUND RECOVERY SYSTEM AND METHOD

(75) Inventors: Marci Norkin, Pasadena, CA (US);
Steven D. Colome, Newport Beach, CA (US)

(73) Assignee: EcoPAS LLC, Irvine, CA (US)

( * ) Notice: Subject to any disclaimer, the term of this patent is extended or adjusted under 35 U.S.C. 154(b) by 375 days.

(21) Appl. No.: 12/476,231

(22) Filed: Jun. 1, 2009

Related U.S. Application Data

(60) Provisional application No. 61/058,913, filed on Jun. 4, 2008.

(51) Int. Cl.
| | | |
|---|---|---|
| *C12G 1/00* | (2006.01) |
| *C12P 7/06* | (2006.01) |
| *C12M 1/36* | (2006.01) |
| *C12M 1/107* | (2006.01) |

(52) U.S. Cl.
USPC ........ 426/15; 435/161; 435/286.1; 435/300.1

(58) Field of Classification Search
CPC .......... A23K 1/06; B01D 1/0047; B01D 1/16; B01D 3/002; B01D 3/346; B01D 5/0087; C07C 31/08; C12M 21/12; C12M 23/52; C12M 29/18; C12M 29/24; C12M 41/18
USPC ............................................... 426/11, 15, 16
See application file for complete search history.

(56) References Cited

U.S. PATENT DOCUMENTS

| | | | | |
|---|---|---|---|---|
| 2,536,994 | A | * | 1/1951 | Cremaschi ...................... 426/15 |
| 4,112,829 | A | * | 9/1978 | Poinsard et al. ................. 99/277 |
| 4,971,813 | A | * | 11/1990 | Strobel et al. ................... 426/51 |

OTHER PUBLICATIONS

Alford, JS. Bioprocess control: Advances and challenges. Computers & Chemical Engineering vol. 30, Issues 10-12, 12, Sep. 2006, pp. 1464-1475.*
Alford, JS. Bioprocess control: Advances and challenges. Computers & Chemical Engineering vol. 30, Issues 10-12, Sep. 12, 2006, pp. 1464-1475.*
Dombeck,KM , Ingram, LO.Ethanol Production during Batch Fermentation with *Saccharomyces cerevisiae*: Changes in Glycolytic Enzymes and Internal pH. Applied and Environmental Microbiology, Jun. 1987, p. 1286-1291 vol. 53, No. 6.*
"Reasonably Available Control Technology Analysis (RACT) for Wine Fermentation, Wine Storage Tanks, and Brandy Aging" 2007 Ozone Plan, San Joaquin Valley Unified Air Pollution Control District, Appendix K, Apr. 30, 2007, pp. K-3, K-13 to K-20, K-40, K-54.

* cited by examiner

*Primary Examiner* — Humera Sheikh
*Assistant Examiner* — Subbalakshmi Prakash
(74) *Attorney, Agent, or Firm* — Wallace G. Walter

(57) ABSTRACT

The present invention provides for passive VOC recovery in the fermentation process that does not affect or minimally affects the conditions within the fermentor vessel and does not affect or minimally affects the conditions within the headspace of the fermentor vessel itself while using the production of $CO_2$ emitted during the fermenting process as the source of driving energy to move a portion of the gaseous/vaporous material in the headspace of the fermentor through an appropriately sized conduit to a chilled surface condensing device to condense the VOCs (principally ethanol) for recovery and to exhaust the $CO_2$ to the atmosphere or to recover the $CO_2$ for other uses. The conduit from the headspace of the fermentor to the condenser is sized to provide a flow restriction in a selected range such that the headspace equilibria are not affected while allowing a portion of the gaseous/vaporous material in the headspace to move through the conduit in response to the generation of the $CO_2$ during the fermentation process.

3 Claims, 11 Drawing Sheets

VOLATILE ORGANIC COMPOUND RECOVERY SYSTEM AND METHOD

CROSS-REFERENCE TO RELATED APPLICATION

This application claims the benefit of U.S. Provisional Patent Application 61/058,913 filed by the inventors herein on Jun. 4, 2008, the disclosure of which is incorporated herein by reference.

BACKGROUND

The present invention relates to the recovery of volatile organic compounds (VOC) and, more particularly, to the recovery of volatile organic compounds associated with the fermentation processes, and, still more particularly, to the recovery of ethanol produced as a consequence of yeast-based fermentation processes associated with the production of wines, beers, brandies, rum, distilled spirits, etc. in which carbon dioxide ($CO_2$) is co-evolved with ethanol (EtOH).

As an example, during the production of wine, a mixture of crushed grapes, juice, and yeast is placed in a fermentation vessel; the yeast metabolizes sugars in the grape juice (known as "must") over a period of several days to one or two weeks at a process temperature of about 60-90° F. During this fermentation period in which the liquid component of the must evolves into the new wine, both EtOH and $CO_2$ evolve in equal molar amounts as a consequence of yeast metabolism. Governed by the chemical properties of solubility, vapor pressures in the headspace, and other chemical and physical properties, the ethanol and the carbon dioxide enter the headspace within the fermentation vessel above the surface of the must. In typical wine-making processes, the ethanol vapor and the $CO_2$ gas escape from the fermentation vessel into the ambient atmosphere during normal venting or when the fermented liquid is subject to inspection/testing and at other points in the production process.

The volume of $CO_2$ evolved during fermentation is a function of the product of the $CO_2$ gas volume per mole, the number of moles of $CO_2$ per liter of liquid, and a temperature term, i.e.,: Volume($CO_2$)=[Volume($CO_2$)/mole]*[moles ($CO_2$)/Liter]*[$F_{temp}$] as presented by Roger B. Boulton, et al., *Principles and Practices of Winemaking* (New York, Springer Science+Business Media, Inc., 1999); assuming a fermentation temperature T of 68° F. (20° C.) and molar and weight values as presented in the following representative equation, about 56 Liters of $CO_2$ per Liter of liquid is evolved (assuming a 24° Brix reduction):

$$= \left[\frac{22.4 \text{ Liter}}{\text{mole}(CO_2)}\right] * \left[\frac{210 \text{ grams}}{\text{Liter}}\right] * \left[\frac{1 \text{ mole sugar}}{180 \text{ grams}}\right] * \left[\frac{2 \text{ moles } CO_2}{1 \text{ mole sugar}}\right] * \left[\frac{273.2 + T(° \text{ C.})}{273.2}\right] \quad \text{EQ 1}$$

FIG. 1 is a graphical representation of the Boulton equation for must in a 50,000-600,000 gallon range and shows potential $CO_2$ emitted in the 400,000 to 4.5 million cubic feet range with a linear slope and is based on the Boulton equation with fermentation at 30° C. (86° F.) and a 23° Brix reduction (or 201.3 grams/Liter).

The EtOH emission factor EF (lbs ethanol lost/1,000 gal of wine made) is given by the formula:

$$EF=(0.135T-5.91)+(B-20.4)(T-15.21)(0.0065)+C \quad \text{EQ 2}$$

where:
T=fermentation temperature ° F.
B=initial sugar content, ° Brix (typical full fermentation reduction is about 20.4° B)
C=0 for white wine and 2.4 lb/1,000 gal for red wine The EtOH emission due to temperature and change in the Brix is given by the formula:

$$\log(E_{lost}/[(S_o-S)^2]=K4-K5/(T+273) \quad \text{EQ 3}$$

where:
$E_{lost}$=ethanol emitted (g/L)
$S_o$=initial sugar concentration (g/L)
S=final sugar concentration (g/L)
T=fermentation temperature (° C.)
K4, K5=constants, 6.682 and 2,552 respectively Of the two emission formulas above, the first (EQ 2) is a representation of the United States Environmental Protection Agency (EPA) formula for red and white wine EtOH emission at a specified starting Brix with the temperature variable, and the second formula (EQ 3) is a representation of the Williams-Boulton formula for EtOH emission from white wine at a specified starting and finished Brix with a temperature variable.

FIG. 2 is a graphical representation of the potential EtOH emission factor EF for must in a 50,000-600,000 gallon range and shows emitted EtOH in the 400 to 5000 lb range for red wine with a linear slope and emitted EtOH in the 200 to 2200 lb range for white wine, also with a linear slope. FIG. 2 is derived from EQ 2 with a 23° Brix reduction.

FIG. 3 is a graphical representation of the potential EtOH emission factor EF for a 100,000 gallon must as a function of temperature showing a range of about 160-350 lbs for white wine in a 54-70° F. range and about 610 to 970 lbs for red wine in a 70-96° F. range. FIG. 3 is also derived from EQ 2.

The loss of gaseous EtOH into the ambient atmosphere is undesirable since EtOH (as well as other VOC emissions from a variety of other industrial, mobile, and natural sources) in the presence of oxides of nitrogen, reacts in sunlight to produce ozone. This has led to regulations in certain wine-producing areas of California to encourage wineries to reduce their EtOH emissions.

A number of attempts have been made to recover the ethanol vapors from the wine-making process and have been recognized as not feasible because they have the potential to jeopardize the quality of the wine produced or are otherwise incompatible with the wine-making process. It is generally recognized that any recovery process must not or may only minimally impact the fermentation process to insure product quality. Thus, recovery systems that change or impact the equilibrium of the fermentation-created conditions in the headspace (temperature, pressures, constituent ratios, etc.) are unacceptable because of the risk to the quality of the final product.

To date, active control systems utilizing thermal oxidation, catalytic thermal oxidation, regenerative thermal oxidation, wet scrubbing (absorption), adsorption vapor recovery, and condensation, refrigeration, and cryogenic systems have been considered untenable in the wine-making system. In an Apr. 30, 2007 report, the San Joaquin Valley Unified Air Pollution Control District, which has adopted the first winery-specific ethanol regulations in the world, has stated, "Currently there is no achieved in practice control technology to control VOC emissions from wine fermentation or brandy aging." and "there is concern that emissions control could contaminate the product or impact wine quality consistency." Based on these concerns, the District "believes that there is no feasible RACT-level control for wine fermentation, wine storage tanks, and brandy aging." Further, a report from the San Joaquin Valley Unified Air Pollution Control District found that the US Environmental Protection Agency's emission control database "contains no examples of controlling wine fermentation emissions."

Traditional methods of emission control have not proven feasible as they risk interference with the natural fermentation process. Of utmost importance for the process is to maintain a friendly environment for the yeast and ensure the integrity of the finished wine product. Any change in the headspace conditions runs the risk of a sub-optimal product and the consequent economic loss in the marketplace.

SUMMARY

A system for passive VOC recovery in the fermentation process that does not adversely affect the conditions within the fermentor vessel and does not affect or minimally affects the conditions within the headspace of the fermentor vessel uses the production of $CO_2$ during the fermenting process as the driving energy source to move a portion of the gaseous/vaporous material in the headspace of the fermentor through an appropriately sized conduit to a chilled condensing device to condense the VOCs (principally ethanol) for recovery as a liquid and to exhaust the $CO_2$ to the atmosphere or to recover the $CO_2$ for other uses. The conduit from the headspace of the fermentor to the chilled condensing device is sized to provide a flow restriction in a selected range such that the headspace equilibria is not affected while directing the gaseous/vaporous material in the headspace to move through the conduit in response to the generation of the $CO_2$ during the fermentation process. Condensation capacity is increased or decreased as appropriate during the fermentation cycle to recover the EtOH from the headspace.

The disclosed system passively harnesses the natural process of fermentation and utilizes its gaseous by-products as the driving force to propel EtOH for its subsequent collection through condensation to accomplish a pollutant-reduction goal while capturing the EtOH, a commercially useful product, and without jeopardizing the quality of the resulting beverage. The natural evolution of $CO_2$ gas from the fermentor functions as the propellant which induces flow to a condensing function or device.

DESCRIPTION OF PREFERRED EMBODIMENTS

Figure 4:
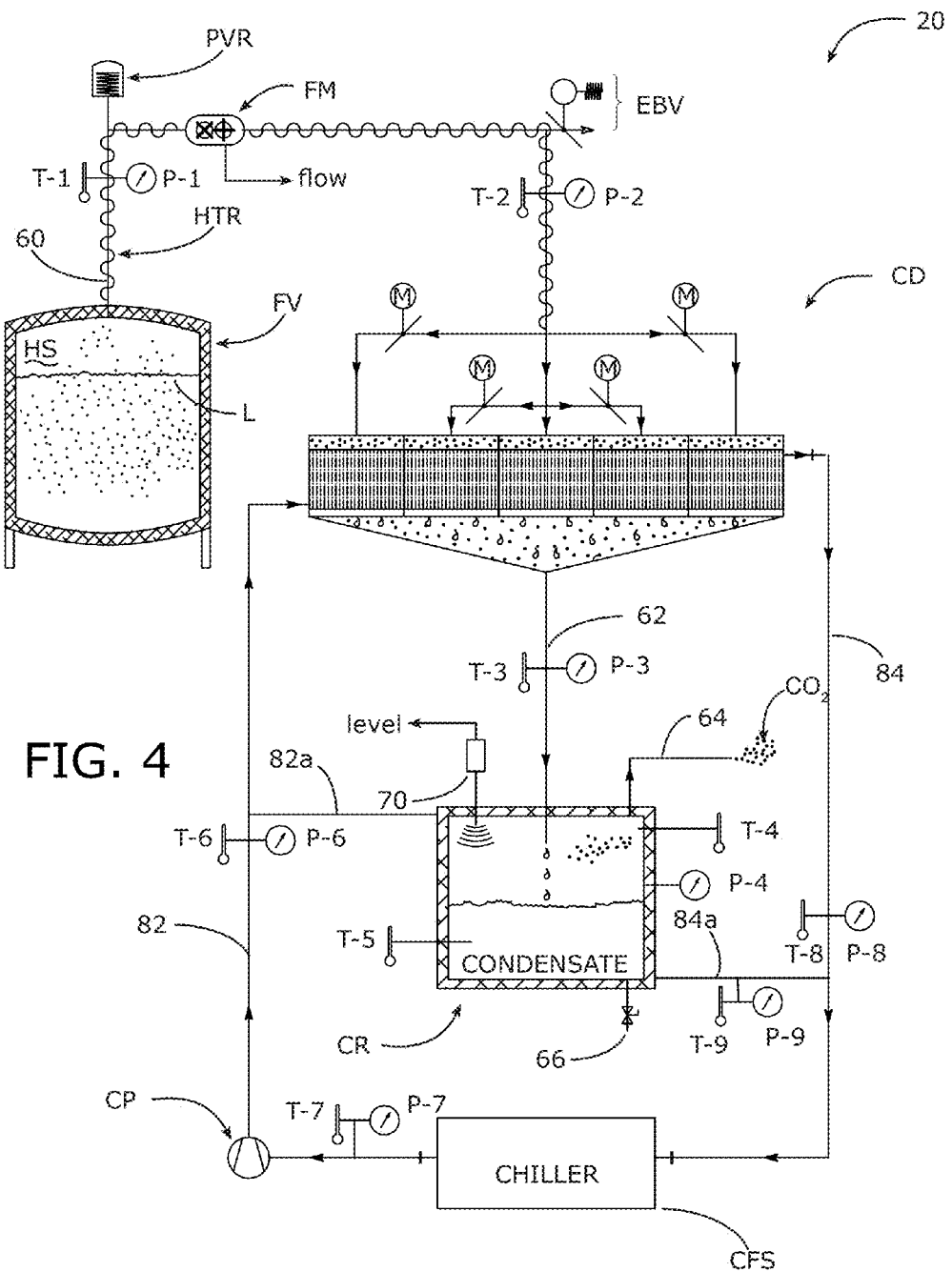
FIG. 4 is a process flow diagram of a representative embodiment of the present invention.

A representative example of a fermentation/recovery system is shown in FIG. 4 and is designated generally therein by the reference character 20. As shown, the principal components of the system 20 include a fermentor tank or vessel FV, a condensation device(s) CD, a recovered condensate container or reservoir CR, a chilled fluid or refrigerant fluid source CFS, and a circulation pump CP for causing the circulation of the chilled fluid or refrigerant through the condensation device(s) CD.

The fermentation vessel FV is typically fabricated from stainless steel, copper, or other suitable materials and typically has a working volume or capacity of up to 600,000 gallons or more. While not specifically shown, the fermentation vessel FV includes various viewing/inspection ports, hatches, and closable openings, as is conventional in this art. In practice, the lower portion of the interior volume of the fermentation vessel FV is filled to some level L with the liquid grape or other fruit extracts, hops, grains, and/or other fermentable feedstocks along with any other materials/additives typically used in the process. A headspace HS is left above the surface of the liquid into which water vapor, ethanol, $CO_2$, and other gases or vapors associated with the fermentation process accumulate; in general, an equilibria is established between the liquid component and the gaseous/vaporous components in the headspace HS for optimal fermentation to yield the highest quality product, particularly in the case of wine.

The condensation device(s) CD typically includes internal passages through which a chilled-fluid (liquid or gaseous) is passed to remove heat from the surfaces in contact with those surfaces chilled by the fluid. As explained in more detail below, a propylene glycol mixture, chilled brine (or an equivalent fluid) at a temperature in the 10° F.-40° F. range can be passed through the condensation device CD to effect the desired condensation.

A tap-off pipe or conduit or bleed-off line 60 extends from a tap-off hole or port (not shown) in the top portion of the fermentation vessel FV to an inlet or inlets of the condensation device CD. As explained below, the bleed-off line 60 accommodates the transfer of gases and/or vapors in the headspace HS as a general function of $CO_2$ production within the fermentor vessel FV.

The connection of the bleed-off line 60 to the fermentor vessel FV can include a cover attached to the fermentor access hatch, a flanged coupling, or other methods to provide a relatively air-tight connection to maintain headspace HS pressure. The bleed-off line 60 is a preferably conventional, EtOH-resistant, food-grade hose with a diameter typically in the 1-5 inch range, scaled to the size of the fermentation vessel; for larger fermentor tanks with a capacity of 600,000-1,000,000 gallons, approximate cross-sectional hose diameters in the six to eight inch range are suitable. The line 60 can have a circular or non-circular inside flow cross-section, the interior walls defining the inside lumen can have varying or non-varying surface roughness characteristics, the inside cross-section can vary significantly with length as a consequence of step-increases or decreases in diameter and varying diameters consequent to the use of varying type of straight and non-straight couplings or fittings, etc. Additionally, the conduit or pipe can be fabricated from a rigid piping, semi-rigid piping having a measure of flexure, and/or flexible piping fabricated from a plastic or elastomeric material. The flow rate through the bleed-off line 60 with time varies as a function of the $CO_2$ production to maintain a desired equilibrium within the headspace HS during those critical periods of the fermentation process so that some of the VOCs, particularly ethanol, can be removed from the process and captured without impacting the quality of the product being produced.

In the fermentation process, the yeast component metabolizes sugars in the starting material with the process proceeding on a day-by-day basis until completion. The fermentation process generates $CO_2$ and EtOH in direct proportion to one another in the liquid must with the gases/vapors in the headspace HS at a temperature of 60-90° F. or so during the process. The production of ethanol and $CO_2$ is directly proportional during fermentation due to yeast metabolism in the must. The release of $CO_2$ and ethanol into the headspace HS is governed by the solubility of each in the must, as well as the relative vapor pressure under non-ideal gas conditions. The rise of $CO_2$ precedes that of EtOH in the headspace HS and functions to carry the EtOH as a co-evolved exhaust vapor through the bleed-off line 60. The volume of emitted $CO_2$ provides an effective source of driving energy since the potential volume of $CO_2$ gas during the course of a full fermentation is approximately 55-58 times ($L_{gas}/L_{fluid}$) that of the starting volume of the must, without secondary volumetric adjustment for water vapor, Boulton, et. al (1999). The functional relation between sugar consumption and $CO_2$ production in yeast fermentation pursuant to the EQ 1 formula is discussed above. In general, a bleed-off line having a flow cross-section sufficient to move gaseous/vaporous components at a pressure of about 0.50 psi is adequate.

Figure 4A:
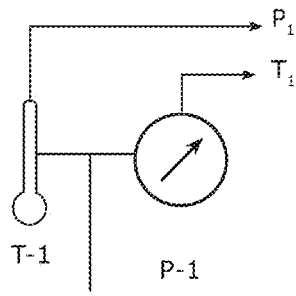
FIG. 4a illustrates a representative pressure/temperature gauge set for providing pressure/temperature information, $P_1$ and $T_1$.

The bleed-off line 60 is instrumented with a temperature sensor T-1 (such as thermistor or thermocouple) to monitor the temperature of the vaporous/gaseous flow from the headspace HS. In a similar manner, a pressure indicator P-1 is used to monitor headspace HS and line pressure and may be used to maintain a pressure lower than the design static pressure limits of the fermentor vessel FV. As shown in representative manner in FIG. 4a, the temperature sensor T-1 and the pressure indicator P-1 can provide electrical outputs $T_1$ and $P_1$ indicative of the sensed temperature and pressure for use in data-logging, data display, and for control functions. One or both outputs can be in analog or digital form and, if desired, any analog outputs can be converted to digital form by appropriate analog-to-digital converting and conditioning circuitry.

A pressure-vacuum relief valve PVR is connected to the bleed-off line 60 and functions as a primary safety device for the fermentor vessel FV. A flow indicator or meter FM connected to the bleed-off line 60 can take the form of a vertically aligned transparent tube with a tapered thru-passage with a "float" that rises with increased flow, or a digital or analog flow meter. An emergency bypass valve EBV, such as a power-actuated damper with fail-safe spring return to open, is designed to vent the flow from the fermentor FV and the bleed-off line 60 should excessive pressure build in the fermentor vessel FV or bleed-off line 60 or in the event of a fermentation tank foam-over or should other safety sensors trigger and therefore cause the damper to open to fail-safe.

Figure 4B:
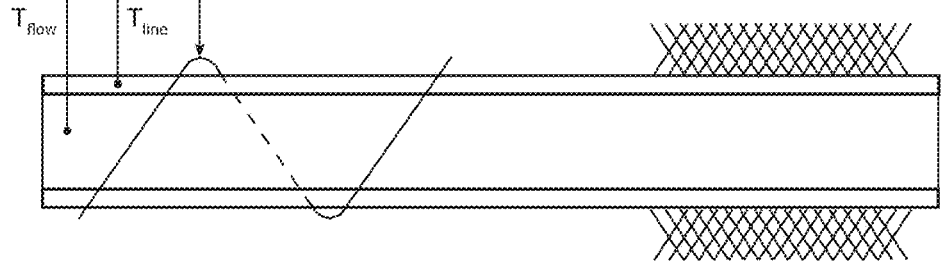
FIG. 4b illustrates the manner in which a heater element is subject to control to effect controlled heating of a bleed-off line.

A heater HTR is provided for the bleed-off line 60 to minimize or prevent condensation in the bleed-off line 60 and is shown in FIG. 4 as a sinuous line enwrapping the bleed-off line 60. Condensation above some minimal amount in the bleed-off line has the potential of changing the equilibrium in the headspace HS that could affect product quality and has the potential to allow liquid EtOH to back flow into the must. The heater HTR may take the form of a resistive wire or tape that is wrapped about the bleed-off line 60. The heater HTR can be 'open-loop' in which the electrical flow through the resistive heating element is set to some temperature to maintain the bleed-off line 60 at some temperature above the temperature of the flow therethrough sufficient to minimize condensation in the bleed-off line 60. In general, maintaining the temperature of the bleed-off line 60 four to six ° F. greater than the temperature of the flow therein should be adequate to minimize condensation in the bleed-off line 60 for most applications, although a larger differential may be indicated in some instances. As shown in the detail of FIG. 4b, active temperature control is also contemplated by which the temperature of the line and the flow therein are sensed and appropriate signals (analog or digital) are provided to a controller, which, in turn, provides appropriate power to the heater HTR to maintain the desired temperature differential. As shown on the right in FIG. 4b in a representative fashion, all or some portion or portions of the bleed-off line 60 can be insulated to conserve heat, especially in those situations where the fermentor vessel FV is located in an exterior location.

In FIG. 4, the heater HTR is shown as a single heater element extending substantially along the entire length of the bleed-off line 60 from the fermentor vessel FV to the first of two branch points prior to the condensing device CD. If desired and depending upon the application, the bleed-off line 60 can be divided into sections and an individual heater HTR can be used for each of the plural sections. In FIG. 4b, the controller may take the form of a 'local' controller or be part of a system-wide controller as explained below in relationship to FIG. 5.

The preferred heater arrangement for the bleed-off line 60 has been described as an electrically powered heater externally wrapped or entwined with the bleed-off line 60. Other arrangements are equally suitable, including the use one or more electrically-powered cartridge heaters in the interior lumen of the bleed-off line 60 to prevent condensation therein. As an alternative, the bleed-off line 60 can be placed in a heat transfer relationship with a source of heated air (from one or more thermostat-controlled forced-air heaters) or heated water to accomplish the heating function.

While heat input to the bleed-off line 60 is preferred, especially in those installations where the fermentor is not housed in a building (i.e., outdoor installations) and/or is otherwise exposed to night-time temperature drops sufficient to cause more than inconsequential condensation in the bleed-off line 60, there may be circumstances in certain installations in which there is no need for any external heat input to the bleed-off line. For example, in certain fermentor configurations, the daily temperature during the fermentation cycle may be somewhat higher than that of the gas/vapor flow in the bleed-off line thus minimizing condensation in the bleed-off line 60 or the bleed-off line may be relatively short such that the quantity of any condensate forming therein is inconsequential, and/or the routing of the bleed-off line to the condensation device is such that most, if not all, condensates formed therein will flow away from the fermentor toward the condensation device.

Figure 4C:
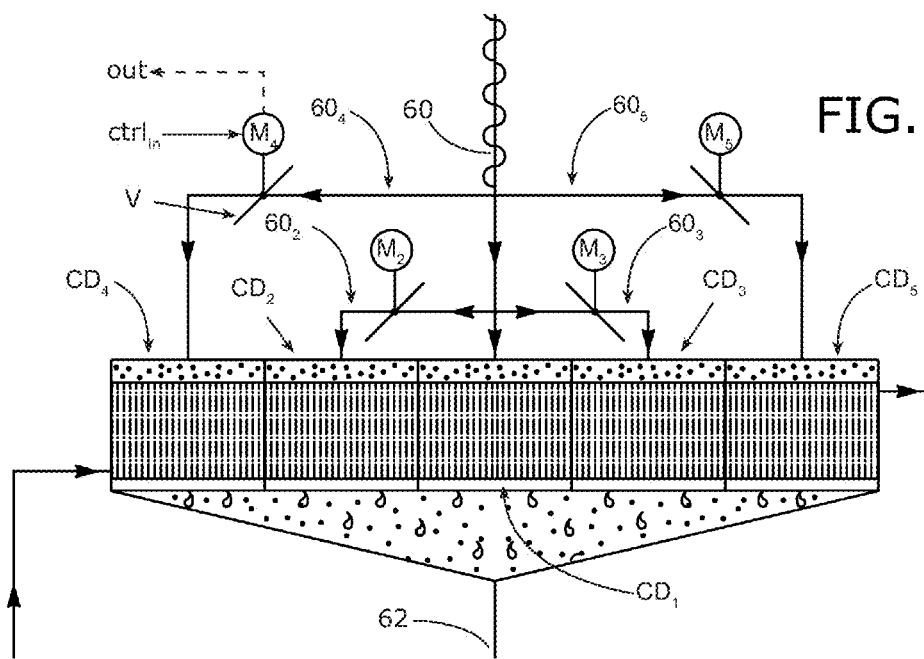
FIG. 4c is an enlarged detail view of a condensation device shown in FIG. 4.

As shown in the detail of FIG. 4*c*, the condensing device CD is shown in a preferred form as having five condenser modules $CD_1$, $CD_2$, $CD_3$, $CD_4$, and $CD_5$. As can be appreciated, additional condenser modules (or fewer condenser modules) can be used depending upon the particular application. In the embodiment of FIG. 4 and as shown in FIG. 4*c*, the bleed-off line 60 branches into lines 60$_4$ and 60$_5$ which enter the respective headspaces of the condenser modules $CD_4$, and $CD_5$. In a similar manner, the bleed-off line 60 further branches into lines 60$_2$ and 60$_3$ which enter the respective headspaces of the condenser modules $CD_2$, and $CD_3$. Thus, that portion of the bleed-off line 60 that connects to the condenser module $CD_1$ and the branch lines 60$_2$, 60$_3$, 60$_4$, and 60$_5$ functions as a type of distribution system or manifold.

Each of the branch lines 60$_2$, 60$_3$, 60$_4$, and 60$_5$ includes respective selectively controllable power-actuated dampers $M_2$, $M_3$, $M_4$, and $M_5$. As represented by the exemplary damper $M_4$ in FIG. 4*c*, each damper $M_n$ includes an input "ctrl in" by which command signals selectively control the damper actuator or motor and, as shown in dotted-line, can include an output signal that outputs the open/close or other operational state of the damper. The various dampers are actuated as needed in response to exhaust flow variation and are used to divert gas flow from the primary bleed-off line 60 to one or more of the available condenser modules $CD_2$, $CD_3$, $CD_4$, and $CD_5$ in order to optimize EtOH collection under the time-varying flow conditions characteristic of natural fermentation. The dampers can be of the type having a movable panel or vane V that is movable between open/close positions in response to their control actuator or motor or can be of the type in which the flow control vane can be moved to one or many available intermediate positions to provide proportionate flow diversion. Regardless of the type of flow control or diverter device used, the controllable dampers M allow for the controlled distribution of the vapor/gas from the fermentor vessel FV to one or more of the condenser modules $CD_2$, $CD_3$, $CD_4$, and $CD_5$ to provide a dynamic re-distribution or re-balancing of the vapor/gas flow from the fermentor vessel FV into the condenser modules throughout the fermentation process. Thus, the condensing capacity of the condensing device CD is variable and can be increased in stages by making one or more of the condenser modules $CD_2$, $CD_3$, $CD_4$, and $CD_5$ available to the flow from the bleed-off line 60 to effect condensing thereof and decreased in stages by closing off one or more of the condenser modules $CD_2$, $CD_3$, $CD_4$, and $CD_5$ from the flow from the bleed-off line 60.

The power-actuated dampers $M_2$, $M_3$, $M_4$, and $M_5$ can be controlled by a central controller, described below, in response to 'flow' signal(s) provided by the flow meter FM and, if desired, by the differential pressure across the condensation device CD as provided by pressure sensors P-2 and P-3 (FIG. 4), and/or a predetermined control profile that reasonably reflects the gas/vapor flow from the headspace HS of the fermentor vessel FV.

The temperature sensor T-2 (FIG. 4) may be used to verify the incoming gas temperature and as a differential temperature indicator across the condenser CD. The pressure sensor P-2 may be used to verify proof-of-flow, monitor inlet pressure to the condenser CD, and, along with the pressure sensor P-3, monitor differential pressure across the condenser CD.

The gases and/or vapors from the headspace HS are conducted via the bleed-off line 60 into the condenser device CD where the ethanol and other VOCs, and all or some of the water content, are condensed out of the gas/vapor stream to yield an ethanol-rich mix of liquid droplets that accumulate in the lower end of the condenser device CD and are passed via line 62 into the ethanol collection tank CR. Once the ethanol, other VOCs, and all or some of the moisture content are "wrung" from the gas/vapor stream, that stream is substantially reduced to $CO_2$ gas. As shown in FIG. 4, the carbon-dioxide exits the ethanol collection tank CR via a vent pipe or conduit 64 for venting to the atmosphere or, alternatively, for recovery for other industrial uses or uses in wine-making processes.

The ethanol collection tank CR is instrumented with a liquid level sensor 70, which can be either of the electronic or mechanical type and which outputs a signal "level" as shown. Additionally, a temperature sensor T-4 outputs the temperature in the space above the level of the liquid, and a temperature sensor T-5 outputs the temperature of the liquid condensate. A pressure sensor P-4 provides pressure information within the ethanol collection tank CR; in general, it is expected that the pressure sensed will be near atmospheric pressure. Lastly, the liquid condensate can be drained from the ethanol collection tank CR via a drain valve 66. In general, the system of FIGS. 4-4*c* will remove a minimum of about 35% and a maximum of over 95% of the ethanol from the flow from the headspace HS and the aggregate flow restriction of the flow path and the condensing device is insufficient to cause normal operating pressures no more than about 0.50 psi (about 14" $H_2O$) rise in the pressure within the fermentation vessel.

If desired, a second chilled-surface condenser can be connected to the $CO_2$ output line 64 (FIG. 4) to receive the $CO_2$ output from the headspace of the condensate collection tank CR to 'wring' any residual VOCs therefrom prior to the release or capture of the $CO_2$ to thereby increase system efficiency.

In FIG. 4, the ethanol collection tank CR is shown in a symbolic fashion; in practice, the ethanol collection tank CR may take the form a sealable canister(s), tank(s), or drum(s) that conforms to industry, state, and/or federal requirements for the secure collection and transport of ethanol by appropriately licensed personnel or agent.

The cooling fluid source CFS contains a chilled fluid (such as brine, glycol, air, nitrogen, etc.) that connects via an external pump CP for causing the circulation of the chilled fluid through a pipe 82 to the condensation device(s) CD and a branch pipe 82*a* to chiller coils in the condensate recovery tank CR to maintain satisfactory conditions within the condensate recovery tank CR. The chilled fluid is returned from the condensation device CD via a pipe 84 and from the condensate recovery tank CR via a branch pipe 84*a* to the chilled fluid source CFS. The chiller/external pump arraignment shown is preferred; however, other arrangements are suitable including an chiller/internal pump arrangement and, as explained below, the chiller coil arrangement of FIG. 9. As shown in FIG. 4, the cooling fluid feed line 82 can be instrumented with temperature/pressure sensors T-6/P-6 and the fluid feed line from the chiller CFS to the circulation pump CP can likewise be instrumented with temperature/pressure sensors T-7/P-7. In a similar manner, the cooling fluid return line 84 can be instrumented with temperature/pressure sensors T-8/P-8 and the fluid return line 84a from the condensate tank CR chiller CFS to return line 84 can be instrumented with temperature/pressure sensors T-9/P-9.

The system 20 of FIG. 4 can be operated in a manual mode in which the operational temperature of the heater HTR (when used) is set and in which the flow or mass flow information from the flow meter FM is monitored with the various dampers $M_2$, $M_3$, $M_4$, and $M_5$ operated to distribute flow to additional condenser modules $CD_2$, $CD_3$, $CD_4$, and $CD_5$ as needed.

Figure 5:
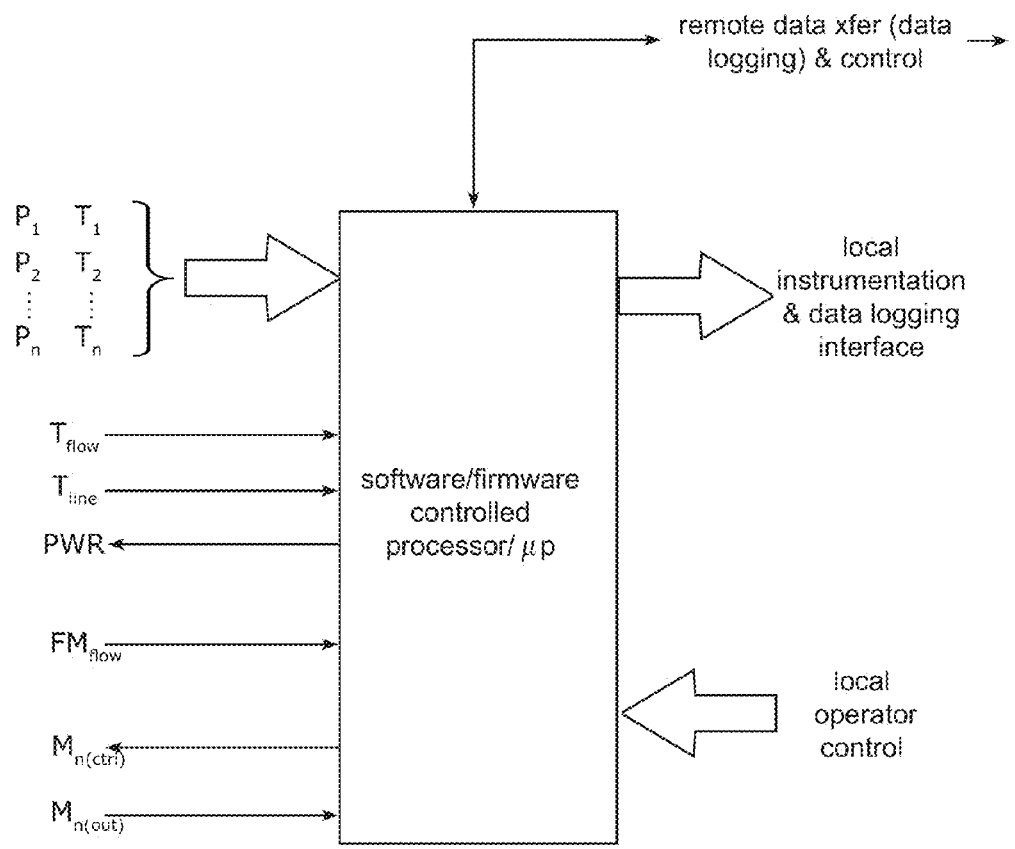
FIG. 5 is a representative or example processor-based arrangement for the semi-automation or automation of the control function(s) of the example disclosed system.

The system 20 is also amenable to semi- or full-automated control using a stored-program processer or microprocessor. For example and as shown in FIG. 5, a software or firmware controller processor or microprocessor (μp) accepts all (or some sub-set) of the $P_1$, $P_2$, ... $P_n$, and $T_1$, $T_2$, ... $T_n$ data, the flow information signal 'flow' from the flow meter FM as well as other inputs including the 'level' signal from the level sensor 70 and the damper position signals 'out' (indicative of the open, closed, or some intermediate operating state of the various dampers) and provides appropriate control signals to the various dampers $M_2$, $M_3$, $M_4$, and $M_5$ to distribute flow to additional condenser modules $CD_2$, $CD_3$, $CD_4$, and $CD_5$ as needed. Additionally, the processor can effect data-logging and provide an instrument readout interface for a system operator. Further, operator controls can be provided to control or override certain aspects of the system operation. For those applications in which multiple fermentors are in operation, some of which may be at different stages in the fermentation process, a telecommunications link can be provided for communicating information to a central location and, if desired, for receiving operational commands therefrom. The telecommunications link can take the form of conventional wired (copper or optical) or wireless links (WiFi) using conventional network protocols (Ethernet, IP, etc.). The software may be hosted on an operating system communicating with other software and/or hardware components in the system.

FIG. 5 shows inputs for the $T_{flow}$ and $T_{line}$ values associated with the bleed-off line 60 heater HTR and a corresponding PWR input for the heater. As mentioned above in relationship to FIG. 4b, the heating of the bleed-off line 60 can be addressed locally or can be addressed in the processor of FIG. 5.

The processor can take the form of one or more firmware- or software-controlled microprocessors or microcomputers (as well as special-purpose processors, including RISC processors), application specific integrated circuits (ASIC), programmable logic arrays (PLA), discrete logic or analog circuits, and/or combinations thereof.

The software or firmware driving the processor can provide output signals to the various dampers M as the quantitative value of the 'flow' signal from the flow meter passes above or increments above various set-points to thereby provide the control signals to the various dampers $M_2$, $M_3$, $M_4$, and $M_5$ to distribute flow to additional condenser modules $CD_2$, $CD_3$, $CD_4$, and $CD_5$ as needed. Conversely, as the quantitative value of the 'flow' signal from the flow meter passes below or decrements below various set-points, the processor can thereby provide the control signals to the various dampers $M_2$, $M_3$, $M_4$, and $M_5$ to proportionately reduce or to cease distributing flow to the various additional condenser modules $CD_2$, $CD_3$, $CD_4$, and $CD_5$.

Figure 6A:
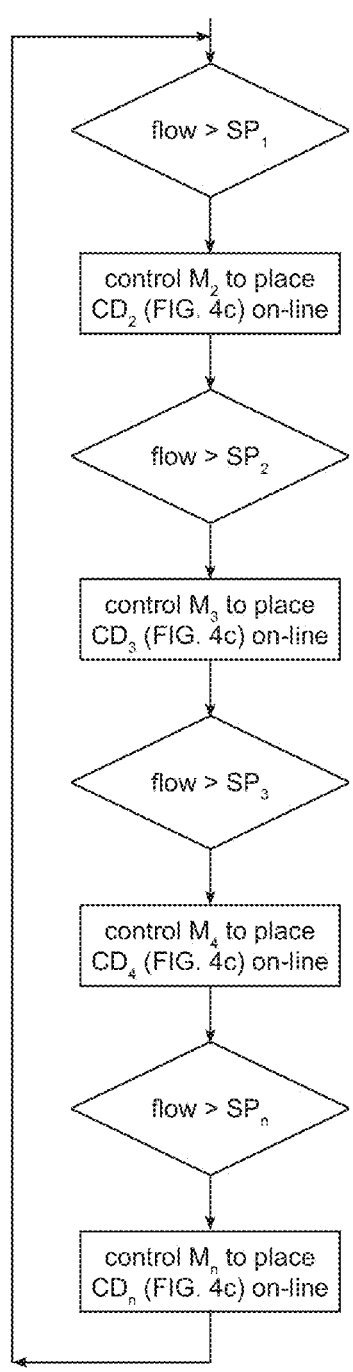
FIGS. 6a and 6b are example flow diagrams showing the manner by which condensation capacity is made available or removed during the fermentation process.
Figure 6B:
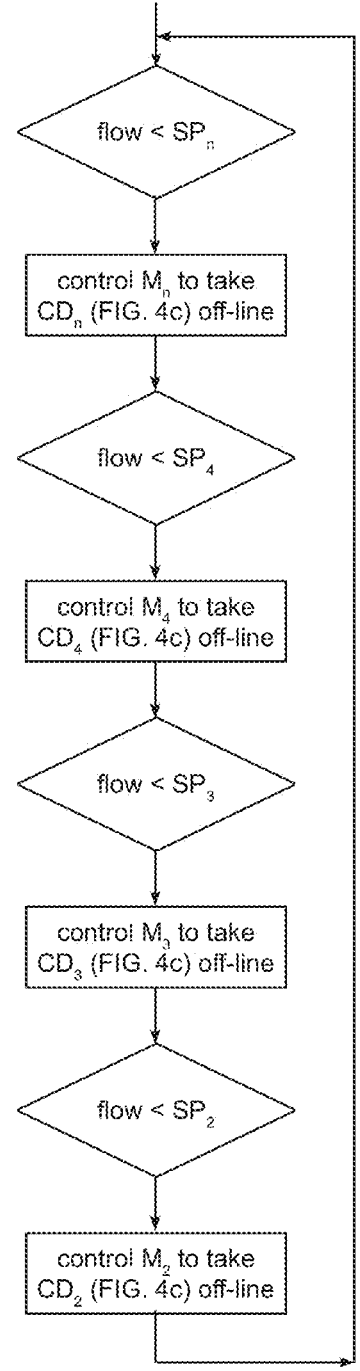

FIGS. 6a and 6b represent exemplary control sequences; in FIG. 6a, set points $SP_1$, $SP_2$, ... $SP_n$ are established with a query presented as to whether the set point has been exceeded or not. As the processor cycles through its flow sequence and in those cases where a set point SP has been exceeded, a control signal is sent to the appropriate damper M to open the damper to place a corresponding condenser module on-line. In FIG. 6b, the processor cycles through the flow sequence and in those cases where the flow value is no longer above the set point SP, a control signal is sent to the appropriate damper M to close the damper M to take a corresponding condenser module off-line.

Figure 11:
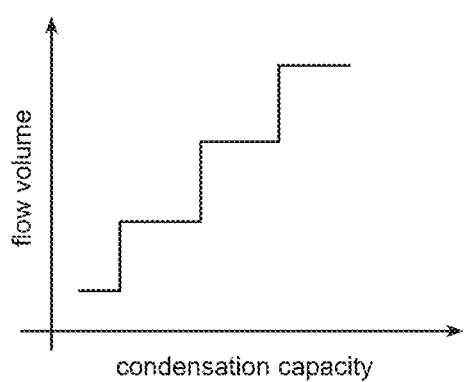
FIG. 11 is an idealized graphical representation of the increase in condensation capacity in the case where on/off dampers or cooling fluid valving is used.
Figure 12:
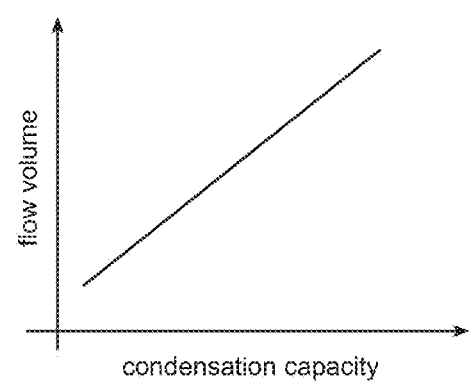
FIG. 12 is an idealized graphical representation of the increase in condensation capacity in the case where proportional flow dampers or chilled fluid valving is used.

While the various dampers M can be operated in an on/off manner to provide an increase or decrease in condensation capacity in a manner consistent with the 'step-wise' graphical representation of FIG. 11, the various dampers can also be operated in a proportional manner to provide a proportional increase or decrease in condensation capacity in a manner consistent with the graphical representation of FIG. 12.

If desired, a measure of hysteresis can be programmed into the control sequence. Thus, a command to any one or more of the dampers M can be delayed until the measured value exceeds a particular set point (FIG. 6a) or decreases below a particular set point (FIG. 6b) for a selected period of time ranging from seconds to minutes.

The set points $SP_n$ can be established as a function of flow (e.g., flow>$SP_n$ or flow<$SP_n$ as shown in FIGS. 6a and 6b), sensed pressure (e.g., P>$SP_n$ or P<$SP_n$), and/or some direct or indirect combination thereof (i.e., f(flow,P)>$SP_n$ or f(flow,P)<$SP_n$) or some other parametric proxy that is functionally related to the gas/vapor flow from the headspace HS during the fermentation process. Additionally, the processor can function in full or partial response to some predetermined control profile that reasonably reflects the gas/vapor flow from the headspace HS of the fermentor vessel FV throughout the fermentation cycle.

Figure 7:
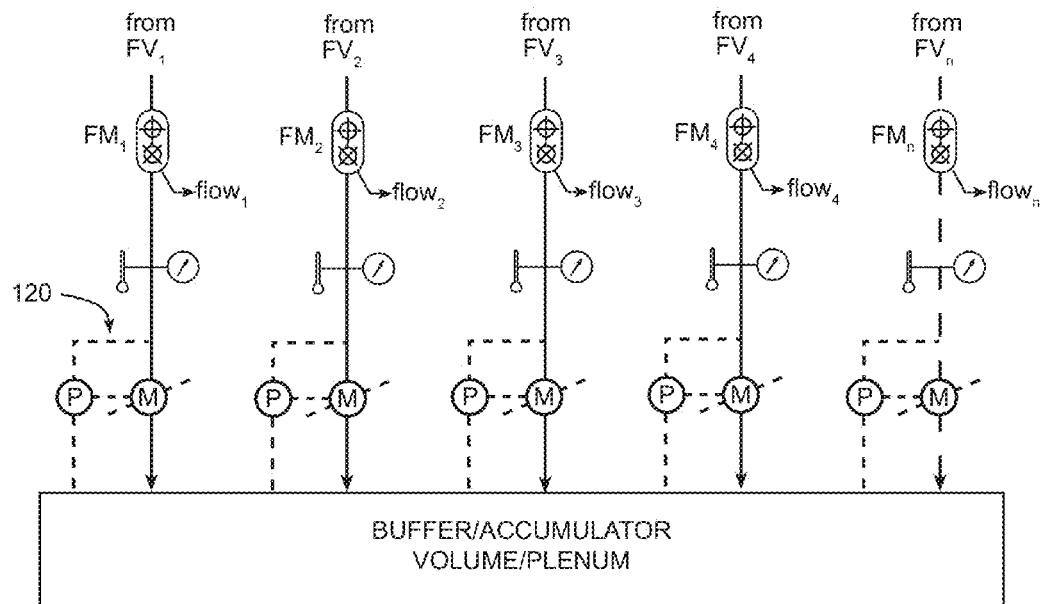
FIG. 7 is a process flow diagram of a representative embodiment suitable for use with one or more fermentor vessels.
Figure 7:
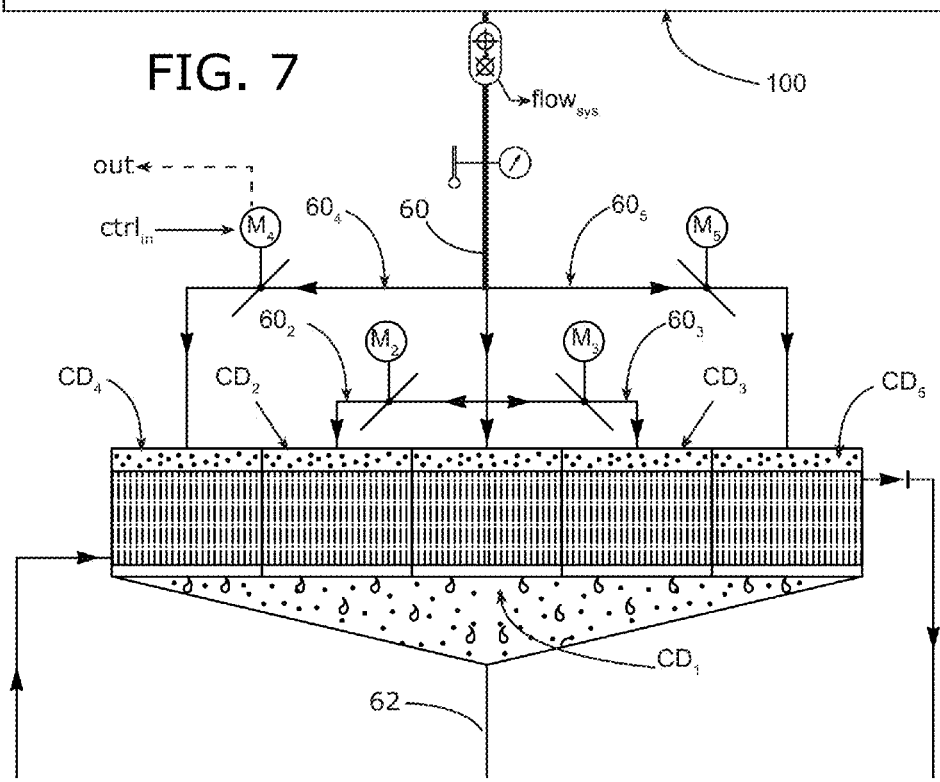

In the embodiment described above, a single fermentor vessel FV supplies gas/vapor from its headspace HS during the fermentation cycle to the condensation device CD. In practice, wineries often have multiple fermentor vessels in simultaneous or near simultaneous operation. In these situations, the output of plural fermentor vessels $FV_1$, $FV_2$, $FV_3$, $FV_4$, ... $FV_n$ can be flowed into the condensation device CD. For example and as shown in FIG. 7, the bleed-off lines from n fermentor vessels $FV_1$, $FV_2$, $FV_3$, $FV_4$, ... $FV_n$ provide their respective gas/vapor flows through flow meters $FM_1$, $FM_2$, $FM_3$, $FM_4$, ... $FM_n$ into a buffer or accumulator plenum 100 with the gas/vapor therein provided to the condensation device CD via a flow meter $FM_{sys}$ in line 60. As shown therein, the various flow meters $FM_1$, $FM_2$, $FM_3$, $FM_4$, ... $FM_n$ provide an output signal $flow_1$, $flow_2$, $flow_3$, $flow_4$, ... $flow_n$, $flow_{sys}$ to the processing system (FIG. 5). Additionally, the various lines are instrumented with pressure and temperature sensors which likewise provide their respective outputs to the processing system as described above.

The organization of FIG. 7 is better suited for those situations in which the plural fermentor vessels are of the same or similar capacity, "charged" with same starting composition and starting volume of must, and the fermentation process started near simultaneously (i.e., within a time period of a few hours) so that the fermentation cycle of each fermentor vessel is substantially in-phase with that of the others. In this manner, the gas/vapor flows of the various fermentor vessels $FV_1$, $FV_2$, $FV_3$, $FV_4$, ... $FV_n$ will be sufficiently equal so that the flow of no one fermentor will be large enough to impede that of the other fermentors and possibly adversely impact the headspace conditions in one or more fermentors. The volume of the buffer plenum 100 should be sufficiently large so that the ramping up of the gas/vapor flows thereinto as balanced by the flow out thereof into the condensation device CD will not cause rapid or sharp pressure perturbations in the system throughout the fermentation cycle.

Figure 7A:
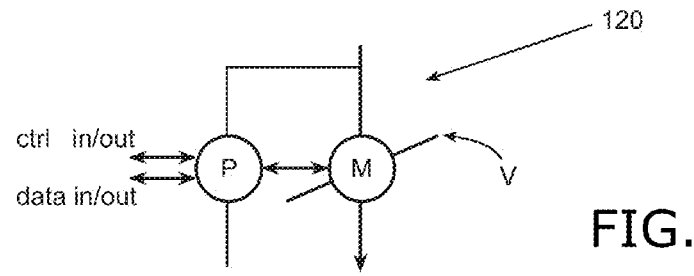
FIG. 7a is a detail schematic view of an optional damper assembly.

As shown in FIG. 7, a damper assembly 120 (shown in dotted-line illustration) may be optionally inserted into each bleed-off line. As shown in FIG. 7a, each damper assembly 120 includes a moveable panel or vane V that controls gas/vapor flow through the bleed-off line, an actuator or motor M that is connected to the vane V to control its position, and a pressure device P that senses pressure on each side of the vane V. Electrical control and data signals ("ctrl in/out" and "data in/out") connect to an external controller (FIG. 5) to control vane V position. The use of damper assemblies 120 may appropriate in some applications in which a measure of pressure balancing is desired.

Figure 8:
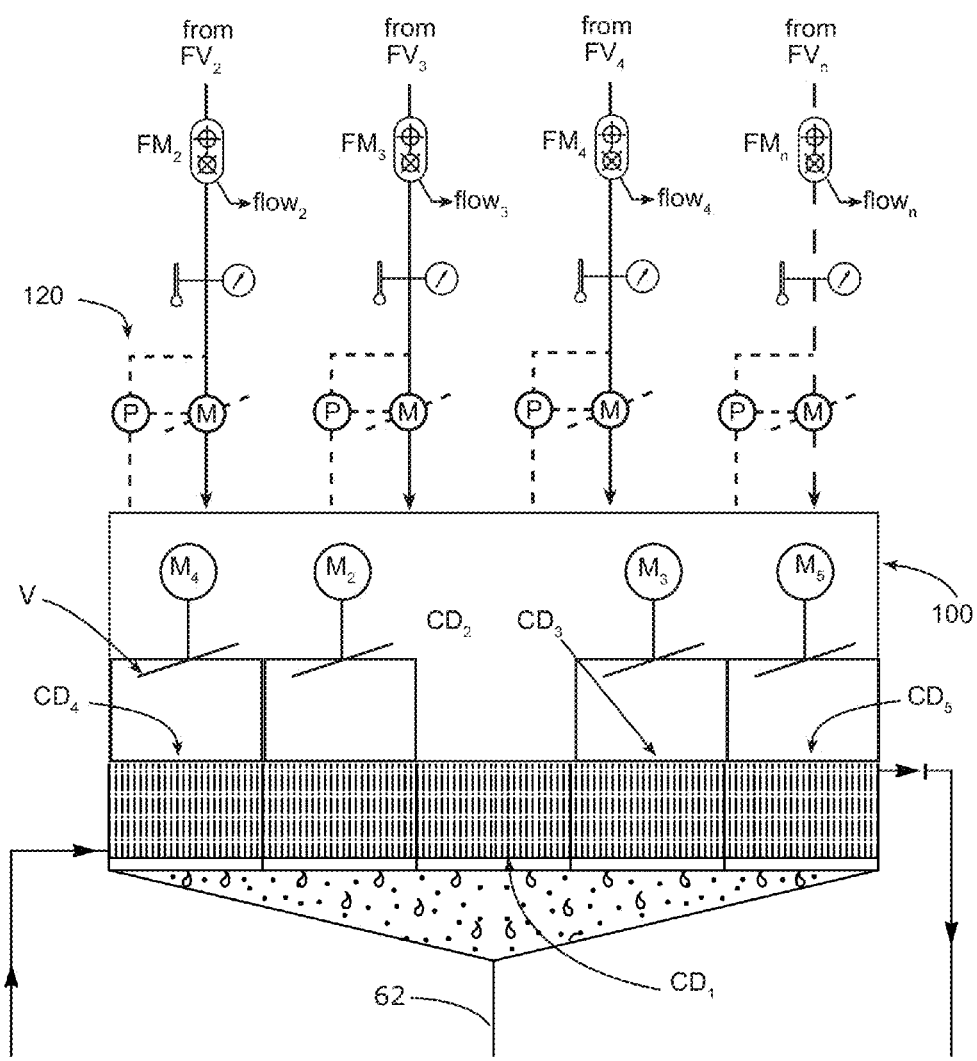
FIG. 8 is a variant of the system shown in FIG. 7.

FIG. 8 represents a variation of the organization of FIG. 7; in FIG. 8, the buffer plenum 100 or buffer volume is integrated into the headspace of the condensation device CD. As shown therein, the gas/vapor flows from the various fermentor vessels FV1, $FV_2$, $FV_3$, $FV_4$, . . . $FV_n$ flow into the now enlarged headspace 100 of the condensation device CD with flow going into the condenser module $CD_1$. Each of the other condenser modules $CD_2$, $CD_3$, $CD_4$, and $CD_5$ includes a movable damper member (such as a flow control vane V) and associated actuator or motor $M_2$, $M_3$, $M_4$, and $M_5$ with the various dampers M controlled in a manner consistent with FIGS. 6a and 6b to provide an increase in condensation capacity as the cumulative gas/vapor flow increases and, conversely, to provide a decrease in condensation capacity as the cumulative gas/vapor flow decreases throughout the fermentation cycle.

As in the case of the arrangement of FIG. 7, damper assemblies 120, shown in dotted-line illustration in FIG. 8, may be used in some applications.

In the embodiments described above, increasing gas/vapor flow from the headspace of the fermentor (FIG. 4) or fermentors (FIGS. 7 and 8) is provided to proportionately increasing condensation capacity (via the additional condensation modules CD). Depending upon the manner by which the dampers M are controlled, an increase or decrease in condensation capacity consistent with the 'step-wise' graphical representation of FIG. 11 or the proportional graphical representation of FIG. 12 can be obtained.

Figure 9:
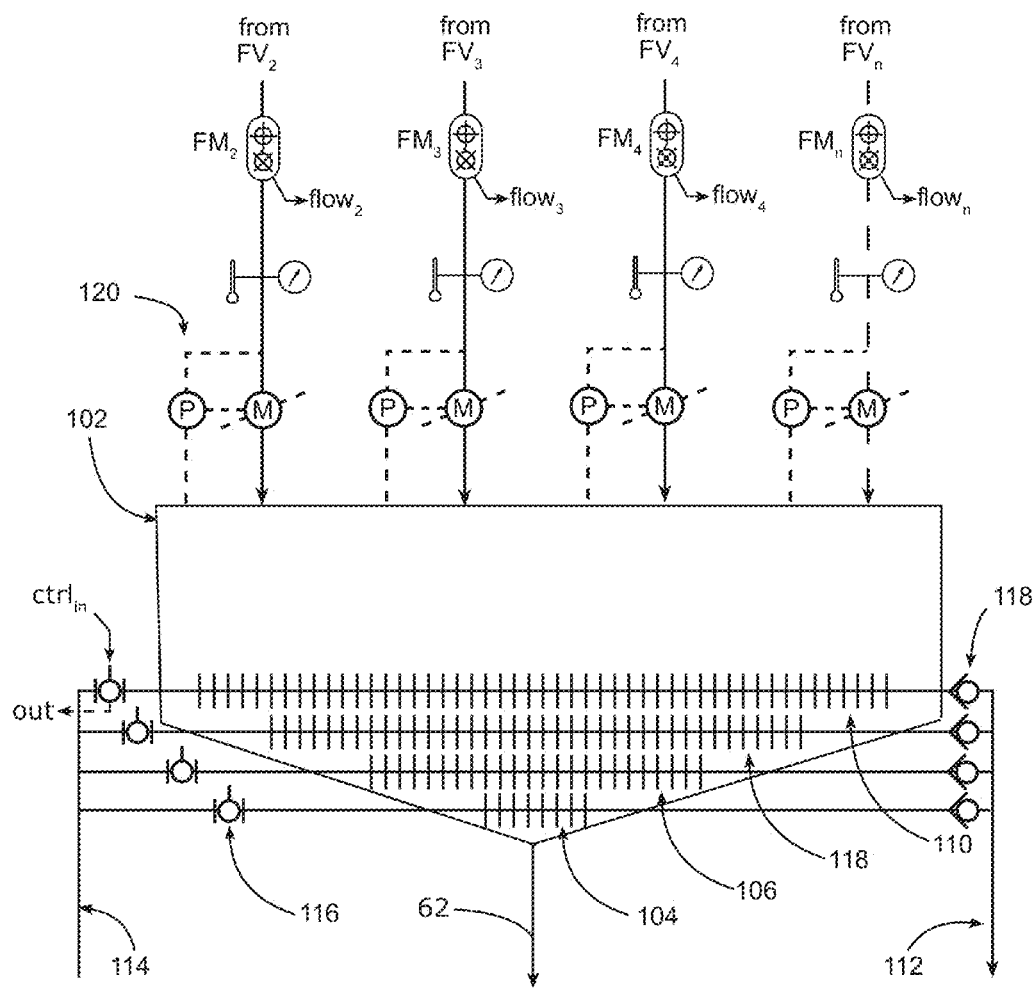
FIG. 9 is a process flow diagram of another representative embodiment suitable for use with one or more fermentor vessels.
Figure 10:
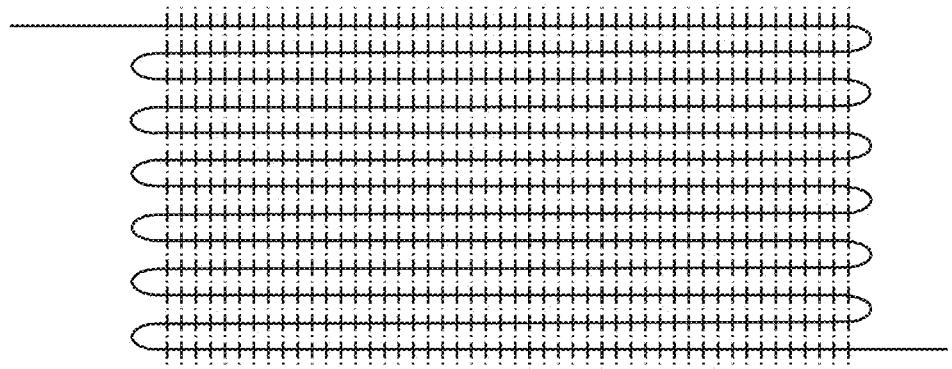
FIGS. 10 and 10a are simplified representations of condensation coils shown FIG. 9.
Figure 10A:
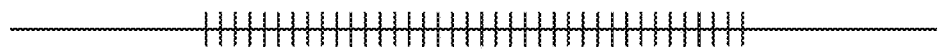

A condensation apparatus variant is shown in FIG. 9 and includes a vessel or plenum 102 into which the gas/vapor flow from the fermentor or fermentors is introduced with the condensed EtOH and the $CO_2$ removed from the lower portion of the plenum 102 into the condensate collection tank. As shown in FIG. 9, the plenum 102 has plural sections or layers of condensation coils 104-110 (as shown symbolically in plan view in FIG. 10a and in side view in FIG. 10b) located above the condensate/$CO_2$ exhaust or effluent conduit 62. The condensation coils 104-110 are connected (on the right in FIG. 9) to a common return line 112 that returns the chilled fluid after it passes through the condensation coil or coils to the chiller CFS. The chilled fluid supply line 114 is connected to each of the condensation coils 104-110 (as shown symbolically in FIG. 9 on the left) with an on/off valve, or, more preferably, a controllable proportional flow valve 116 that accepts a input control signal ctrl to set the valve at a selected ON state (maximum flow) and an OFF state (no flow) state or some intermediate state therebetween. If desired and as an option, each flow valve 116 can include some type of position indicator that provides a return signal 'out' to the controller indicating the currently set flow state. Additionally, backflow preventer valves or devices, as represented at 118 can be used to prevent chilled fluid exhausting from one condensation coil from entering one or more of the other condensation coils.

The system of FIG. 9 processes the flow volumes $FV_n$ from the various fermentors or some parametric proxy therefor (i.e., pressure or the stage of fermentation) to provide information to the controller to progressively increase the condensation capacity by flowing more chilled fluid through particular condensation coil as well as through successive condensation coils 104-110. By increasing the chilling capacity as some function of the cumulative flow volume, an approximate equilibrium is maintained between the gas/vapor inflow into the plenum 102 and the liquid EtOH condensate that is 'wrung' therefrom and the $CO_2$ removed from the plenum 102.

As in the case of the arrangement of FIGS. 7 and 8, damper assemblies 120, shown in dotted-line illustration in FIG. 9, may be used in some applications.

While the system described changes condensation capacity as a function of some parametric value, in some applications where experience shows a certain level of fermentation process predictability with time, it may be desirable to pre-program the changes in condensation capacity with time from the start of the fermentation process and/or pre-program the changes in condensation capacity to correspond with the various stages of the fermentation process and do so with or without consideration of the flow volumes, pressures, etc.

In the case where the valves 116 are bi-state ON/OFF valves, the relationship between increased flow volume and increased condensation capacity can be represented graphically in FIG. 11 as a 'step-wise' function, and, where the valves 116 are proportional valves, the relationship between increasing flow volume and increasing condensation capacity can be represented graphically as a proportional relationship in FIG. 12.

As can be appreciated, the system is sized to stay within a safety factor for allowable fermentor pressure in a closed winery fermentor, where common art has relief valves PVR typically set at about 0.85 psi (or 24" WC). The system 20 as designed is sized to allow for a calculated maximum instantaneous flow rate for a given fermentor tank size, as current art, and to allow pressure build-up of no more than about 0.50 psi (or 14" WC). Major contributors to static pressure in the system are primarily the condenser CD, the size and length of the bleed-off line 60, and smoothness of internal surfaces throughout the system. Other factors include inlet and outlet losses, static effects of fittings, temperature, and the gas/vapor density. As can be appreciated, the system is usable in situations in which the pressure build-up is greater than the above described 0.50 psi (or 14" WC).

The system operates at extremely low-pressure for an emission control system, using the emitted $CO_2$ to provide the driving energy to push flow through the collection system. An advantage of the low pressures characteristic of this system is that premature in-line condensation is minimized, thereby greatly reducing the possibility that condensate will flow back into the fermentor vessel FV and affect the quality of the product. In the described system, the condenser CD produces the greatest static pressure drop in the system and is therefore the controlling element; while the conduit sizing and length are of secondary importance in their contribution to static pressure. For the design of any specific application, turbulence and Reynolds Number is calculated throughout the system, but serves primarily as a secondary check for the maximum instantaneous design flow condition.

Gas/vapor-flow volumes through the system change temporally, starting with zero flow at the start of fermentation and rising to a maximum flow rate. As sugars are consumed in the must, the gas/vapor-flow volumes diminish until fermentation is complete. The system is sized to accept the maximum instantaneous flow rate, in addition to the variable flow and exhaust gas composition encountered during the fermentation cycle.

Initially and when the must is first inoculated with yeast, the fermentation activity is minimal and most of the evolved $CO_2$ and EtOH are dissolved in the must. Flow out of the condenser CD only begins after fermentation has proceeded for a period of time and therefore a decision must be made about when to start EtOH collection. A reasonable practice is to initiate use of the device within 24 hours following yeast inoculation, or by the time there is a 1° Brix reduction, a 2° F. rise in must temperature, or an EtOH concentration in the must that exceeds 3%, whichever occurs first and as in this art, depends on the measurements normally taken by the winemaker. This practice will ensure that the operation of the system does not interfere with the initial aerobic phase of fermentation and that collection is initiated before a significant amount of EtOH has escaped collection. An additional advantage of the low pressures in this system is reduced premature in-line condensation that might cause condensate to flow back to the fermentor vessel FV.

Average conduit velocities are designed in the system to be approximately 1000-3000 fpm. Because of static pressure limitations, as described above, the system and conduit velocities should not exceed 4000 fpm and ideally should operate nearer an average of 1500 fpm. Velocities in excess of 4000 fpm typically result in excessive static pressure that may cause premature in-line condensation or an excessive buildup of static pressure. Initial flows may be below 1000 fpm; however, flows will quickly rise above 1000 fpm as $CO_2$ emissions begin to increase during fermentation. Once fermentation flows in excess of 1000 fpm are attained, the target range of around 1500 fpm is maintained by selected operation of the various dampers $M_2$, $M_3$, $M_4$, and $M_5$ to distribute flow to additional condenser modules $CD_2$, $CD_3$, $CD_4$, and $CD_5$ as needed to maintain static pressures, as described herein in relationship to FIGS. 4, 7, and 8 or selected increases or decreases in condensation capacity as described in relationship to FIG. 9, The system is designed to reduce the potential for premature condensation of EtOH in the bleed-off line 60 by use of the heating feature, described above. The gas-vapor mixture exiting the fermentor vessel FV is maintained at a temperature somewhat above that of the headspace HS by the heated bleed-off line 60, sufficient to prevent or reduce in-line condensation. The temperature of the bleed-off line 60 is preferably regulated at or slightly above headspace HS temperature to thereby minimize the cooling demand on the condenser CD and therefore minimize energy use.

That portion of the bleed-off line 60 that extends into the condenser CD functions as a distribution manifold that transfers gases evolved from the fermentor vessel FV to the condenser CD modules via the various branch lines. As the gas pressure increases in the manifold portion, the pressure sensing device P-2 provides an output sufficient to command or trigger a power-actuated shut-off damper $M_n$ to open at a predetermined pressure. This newly opened branch of the manifold portion will reduce the bleed-off line 60 pressure, fermentor HS headspace pressure, and the velocity through the condenser CD to maintain the desired maximum headspace HS pressure and maximum effective design velocity and pressure through the individual condenser modules $CD_1$, $CD_2$, $CD_3$, $CD_4$, and $CD_5$ as needed. The manifold portion is designed with sufficient branch conduits and condenser modules $CD_n$ to efficiently handle the maximum calculated gases evolved from the fermentation process plus some safety factor. As the pressure continues to increase, additional power-actuated damper(s) $M_n$ will open to distribute the gas/vapor thereby decrease the pressure. Conversely, as the pressure from the fermentor vessel FV decreases to a predetermined pressure, the pressure sensing device P-2 will trigger the appropriately power-actuated damper(s) $M_n$ to close, thereby increasing the pressure in the manifold portion and maintaining a desired minimum design velocity through the condenser modules $CD_n$.

In some applications the flow of $CO_2$ and EtOH over the chilled-surfaces of the condensing device may result in laminar flow at the vapor/chilled-surface interface. In some applications, it may be desirable to limit the formation of laminar flow regions to improve heat transfer therebetween and thus improve condensation efficiencies. Laminar flow regions can of prevented from forming or dissipated after formation by providing the chilled-surfaces with sufficient surface roughness, spine-like projections, projecting edges, grooves, channels, etc. to prevent, minimize, or dissipate laminar flow at the vapor/chilled surface interface. If desired, turbulence can be introduced by a separate fan-like device or an air-flow "stirring" device.

If desired, further steps can be taken within the plenums described above to enhance the transfer of the EtOH into a liquid form. For example, a high-pressure, low-volume water injector(s) can spray a very fine water fog into the plenum to (a) pre-cool the $CO_2$ and EtOH flow and (b) adsorb ethanol vapor. In some applications, it may be desirable to introduce a minimal amount of water or other liquid to slightly dilute the collected ethanol to thereby enhance the capture efficiency. The addition of a fluid spray would be suitable where emission control and offset credits are paramount.

Figure 1:
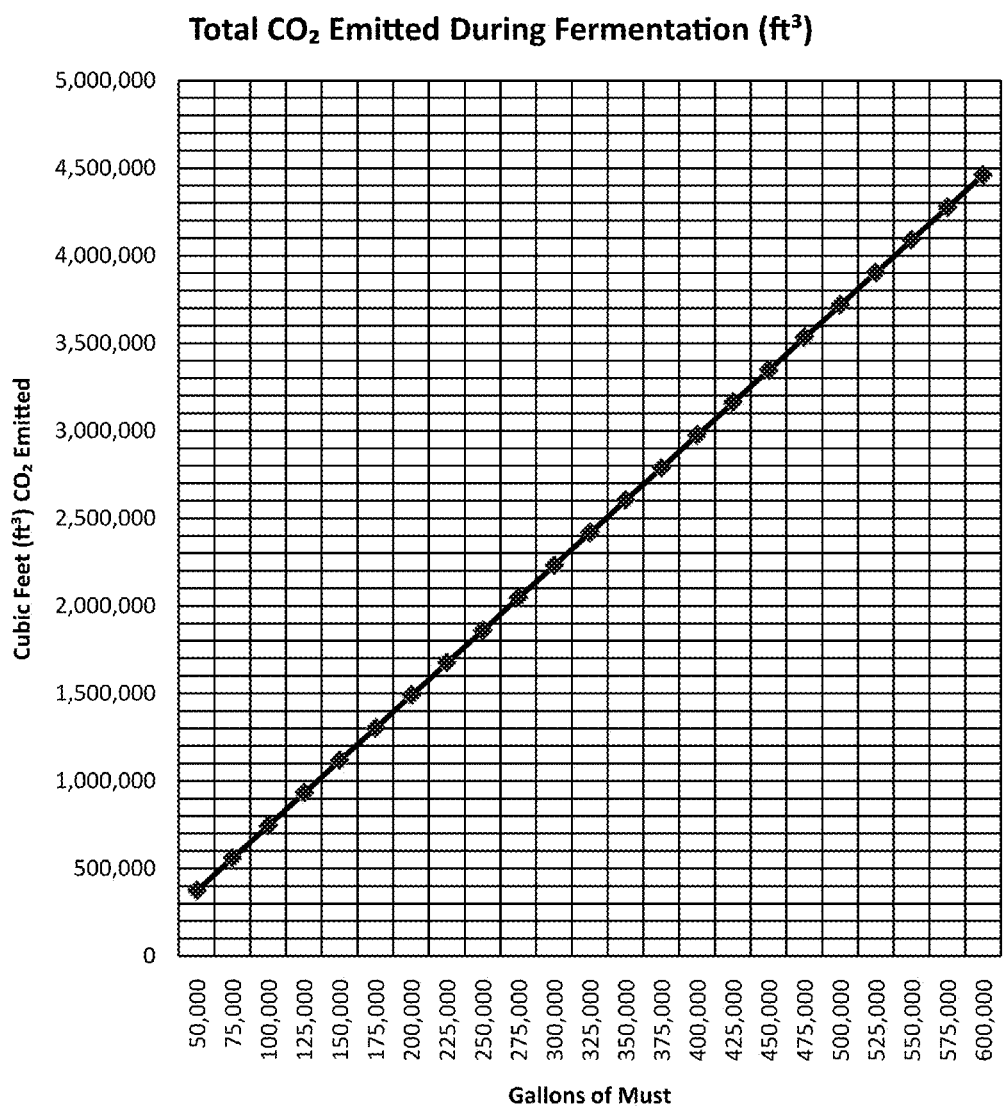
FIG. 1 is a graphical representation of $CO_2$ emission pursuant to the Boulton equation for must in an approximate 50,000-600,000 gallon range and shows emitted $CO_2$ in the 400,000 to 4.5 million cubic feet range.

In the process of natural fermentation, $CO_2$ and EtOH are co-evolved into the must in equal molar amounts as described above. However, the release into the fermentor headspace HS and to the atmosphere is governed by physical and chemical properties of the two compounds in the liquid must, the air/gas interface, and the open atmosphere. Much of the $CO_2$ will ultimately be emitted into the headspace HS and to the atmosphere, with the potential amount released over an entire fermentation cycle given by the Boulton formula discussed above and which was used to generate the linear plot in FIG. 1 showing the total volume, expressed in standard cubic feet (scf), for the typical range of fermentor capacities that the described system is designed to cover. FIG. 1 is based on a typical wine-grape fermentation with approximately a 20 degree Brix reduction in sugar content during fermentation. It is the substantial volume of $CO_2$ released that provides the driving energy to passively "push" the EtOH—$CO_2$ gas/vapor mixture through the conduits and condenser.

Figure 2:
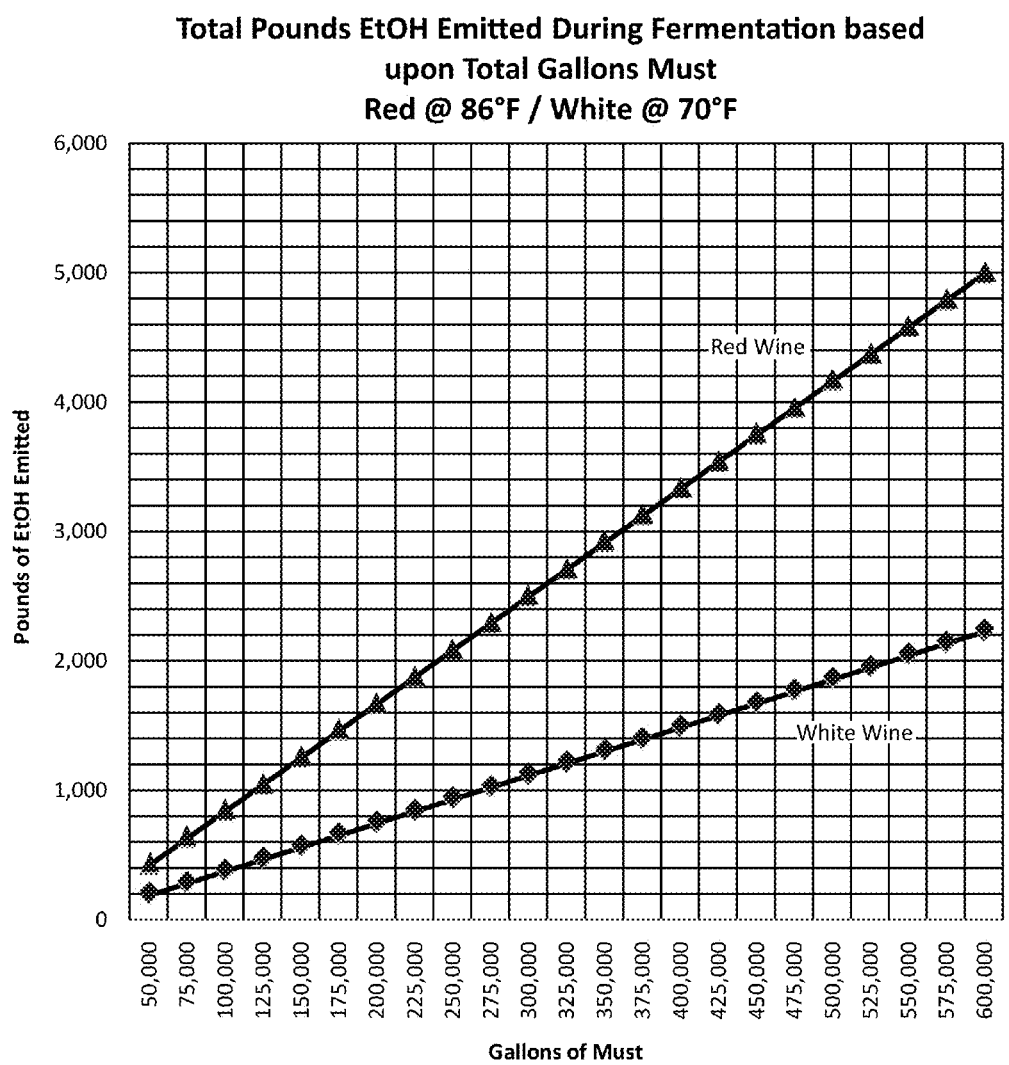
FIG. 2 is a graphical representation of the EtOH emission factor EF for must in an approximate 50,000-600,000 gallon range and shows emitted EtOH in the 400 to 5000 lb range for red wine and emitted EtOH in the 200 to 2200 lb range for white wine.
Figure 3:
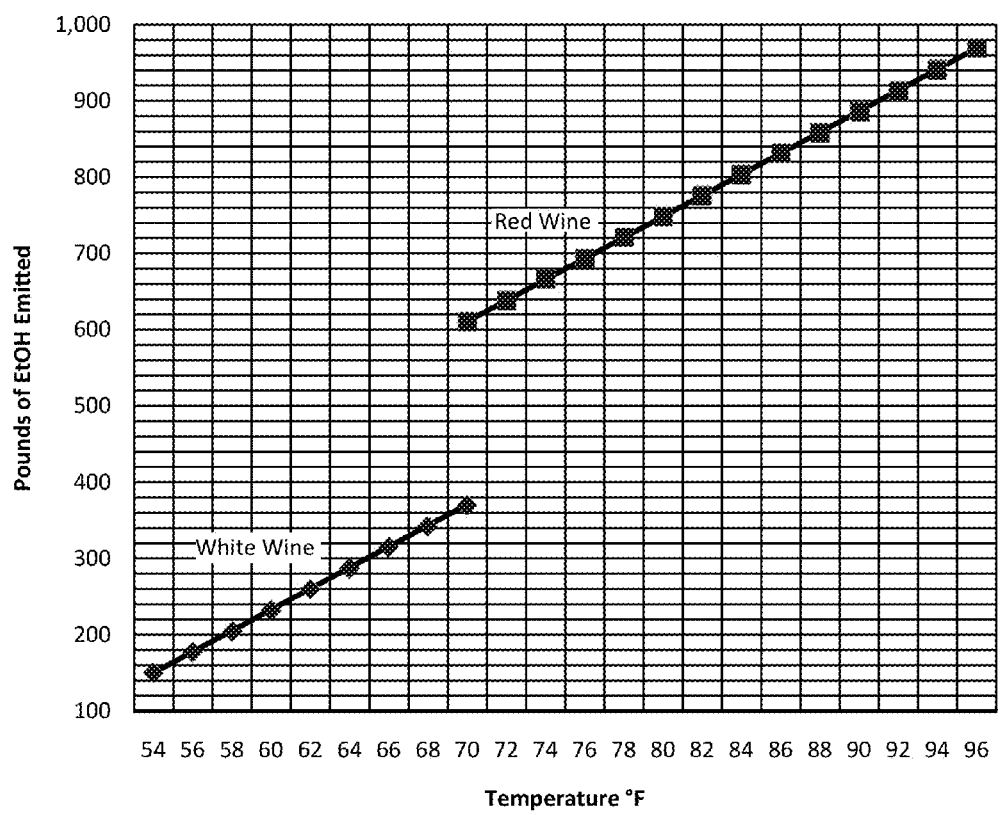
FIG. 3 is a graphical representation of EtOH emissions based upon 100,000 gallon must as a function of temperature showing a range of about 160-380 lbs for white wine in a 54-70° F. range and about 610 to 970 lbs for red wine in a 70-96° F. range.

Release of EtOH to the atmosphere is more complicated than that of $CO_2$ due to the relatively high solubility of the alcohol in the liquid must. Emission of EtOH is governed, among other factors, primarily by the temperature of the fermentation, with hotter fermentations causing greater release of EtOH into the headspace. White wine is generally fermented at lower temperatures than red as illustrated in FIG. 3 for a typical fermentation of red and white wine, both having similar sugar consumption. Another significant factor affecting emission of EtOH is the presence of a solid grape skin cap (known in the industry as pomace) that floats to the top of the must, as is typical in fermentations of red wine. The cap is also responsible for causing temperature inhomogeneities within the fermentor due, in part, to a higher concentration of yeast collecting in the cap, leading to higher temperatures in the must-headspace interface. FIG. 2 illustrates for different volumes of must, the total release of EtOH for red and white wines, accounting for the combined effect of the typically higher red wine fermentation temperatures and the influence of the cap present during red wine fermentation.

Other factors influencing real-time release of EtOH and $CO_2$ include stirring of the must, punching down the grape skin cap, and the stage of the fermentation process.

The following examples are representative of system performance.

EXAMPLE 1

Example I demonstrates capture of EtOH emissions with $CO_2$ as a carrying vehicle from a distilled spirits solution.

A series of six (6) experiments were performed with three different distilled spirits through which $CO_2$ was dispensed; Tequila, Rum, and Vodka. The solutions were heated between 72° F. and 100° F. in a 10 L vessel and compressed $CO_2$ was dispensed through three stainless steel 0.5-micron bubblers to simulate $CO_2$ evolution from fermentation. A glass condenser column with a chilled water jacket was utilized for condensing the vapor emitted from the test vessel with varying cooling water temperature ranging from 32° F. to 42° F.

The results of the experiments showed that EtOH was successfully captured along with water and the base solution esters. Condensates ranged from 30.7 to 73.1% EtOH.

EXAMPLE 2

Example 2 verifies the capture of EtOH emissions with $CO_2$ as a carrying vehicle from a red wine solution at a lower alcohol level than in Example 1.

A series of three experiments were performed utilizing red wine with varying levels of EtOH (from 11.5 to 12.4%). The wine solutions were heated to between 72° F. and 83° F. in a 10 L vessel and compressed $CO_2$ was dispensed through three stainless steel 0.5-micron bubblers to simulate $CO_2$ evolution from fermentation. A glass condenser column with a chilled water jacket was utilized for condensing the vapor emitted from the test vessel with varying cooling water temperature ranging from 32° F. to 45° F.

The results of these experiments showed that EtOH was successfully captured along with water and wine esters.

EXAMPLE 3

Example 3 demonstrates capture of EtOH emissions from a grape must fermentation with naturally evolved $CO_2$.

A 15-gallon fermentation was performed in a high density polyethylene (HDPE) fermentor. The base grape must Brix was increased to 22° B by adding sugar and then inoculated with *saccharomyces cerevisiae* yeast to induce fermentation. The fermentation was allowed to increase in temperature naturally from 70° F. to 83° F. and observed over 5-days by hourly recordings of the instrumentation. A glass condenser with a chilled water jacket was utilized for condensing the evolved vapor from the fermentation with varying cooling water temperature ranging from 30° F. to 54° F.

The results of the experiment showed that EtOH could be successfully captured from a grape must fermentation along with water and wine esters by using the naturally evolved $CO_2$ as the carrying agent.

EXAMPLE 4

Example 4 demonstrates capture of EtOH emissions from an increased volume grape must fermentation with naturally evolved $CO_2$.

A 62-gallon fermentation was performed in a high density polyethylene (HDPE) fermentor. The base grape must Brix was increased to 23° B by adding sugar and then inoculated with *saccharomyces cerevisiae* yeast to induce fermentation. The fermentation was allowed to increase in temperature naturally from 70° F. to 75° F. and observed over 10-days with data-logging instrumentation and manually verified by logging and testing on a scheduled basis. A glass condenser with a chilled water jacket was utilized for condensing the evolved vapor from the fermentation with varying cooling water temperature ranging from 14° F. to 40° F.

The results of the experiment showed that EtOH could be successfully captured from a grape must fermentation along with water and wine esters by using the naturally evolved $CO_2$ as the carrying agent.

EXAMPLE 5

Example 5 verifies the capture of EtOH emissions from a grape must fermentation with naturally evolved $CO_2$ with an elevated initial must temperature.

A 75-gallon fermentation was performed in an insulated high density polyethylene (HDPE) fermentor. The base grape must Brix was increased to 22° B by adding sugar and then inoculated with *saccharomyces cerevisiae* yeast to induce fermentation. The base grape must was inoculated at a starting temperature of 79° F. and then was allowed to increase in temperature naturally from 79° F. to 97° F. and observed over 8-days with data-logging instrumentation and manually verified by logging and testing on a scheduled basis. A glass condenser with a chilled water jacket was utilized for condensing the evolved vapor from the fermentation with varying cooling water temperatures ranging from 19° F. to 26° F.

The results of the experiment showed that EtOH could be successfully captured from a natural fermentation along with water and wine esters by using the naturally evolved $CO_2$ as the carrying agent. In this experiment, EtOH production and observed yeast propagation decreased significantly as the naturally elevating temperature of fermentation approached 95° F.; EtOH emission and observed yeast activity was minimal above 95° F. and was not regained after the temperature dropped below 95° F.

The collected condensate contains alcohol content appropriate for a high-quality distilled alcoholic spirit (66-87 proof) resembling a liqueur, cognac, or brandy and containing the flavor and aroma characteristics of the initial starting material with a high perceived concentration of light floral aromatics. The collected condensate can be suitable as distilled alcoholic spirit or a pre-cursor distilled alcoholic spirit subject to further processing (i.e., alcohol-content adjustment, flavor adjustments, etc.) to result in a finished product.

While the various embodiments have been described in the context of grape-based starting material for the fermentation thereof into a wine product or a precursor wine product subject to further processing, the various embodiments can use various other starting materials including various fruits (such as plums, cherries, peaches, apples, various types of berries, etc.) and various other non-fruit starting materials including rice, corn, potato, etc. to produce brandies, wine, wine precursors, or wine-like products as well as sugar cane juice, various syrups, molasses, etc. to produce rum or rum-like products.

As will be apparent to those skilled in the art, various changes and modifications may be made to the illustrated embodiment of the present invention without departing from the spirit and scope of the invention as determined in the appended claims and their legal equivalent.

The invention claimed is:

1. A process for the recovery of volatile organic compounds present in the headspace of a batch-type fermentation vessel as a distilled alcoholic liquid condensate in which a starting material in the fermentation vessel is subject to a yeast-based metabolic processing cycle to yield a fermented beverage where quantities of $CO_2$ and EtOH vapor are produced therein during which increasing quantities of $CO_2$ and EtOH vapor are produced during an initial part of the processing cycle and decreasing quantities of $CO_2$ and EtOH vapor are produced during a latter part of the processing cycle, any pressure increase or decrease within the headspace of the fermentation vessel substantially related to the increase or decrease in the quantities of the $CO_2$ and the EtOH vapor produced therein during the yeast-based metabolic processing cycle, comprising the steps of:

connecting a flow pathway between the headspace of the fermentation vessel and a controllable variable-capacity condensation device for flowing at least a portion of the $CO_2$ and the EtOH vapor from the headspace therethrough and into the condensation device, the condensation device having a condensing capacity sufficient to condense at least 35% of the EtOH vapor passing therethrough into a liquid, the flow rate of the $CO_2$ and the EtOH vapor from the headspace of the fermentation vessel through the vapor flow pathway being responsive to the quantity of at least the $CO_2$ produced during the yeast-based metabolic processing cycle in the fermentation vessel, the aggregate flow restriction of the flow path and the condensation device insufficient to cause no more than about a 0.50 psi rise in the pressure within the fermentation vessel, the variable-capacity condensation device controlled by a stored-program controlled processor in response a sensor responsive to the flow rate in the flow pathway, supplying heat sufficient to raise the temperature of the major portion of the surfaces of the flow pathway in contact with the $CO_2$ and the EtOH vapor flowing therethrough to a temperature at least four to six degrees F. greater than the temperature of the flow therein;

condensing at least a portion the EtOH vapor into an alcoholic liquid condensate, increasing the condensing capacity of the condensation device in incremental steps as a function of an increasing quantity of the $CO_2$ and the EtOH vapor produced during the yeast-based metabolic processing cycle, decreasing the condensing capacity of the condensation device in decremental steps as a function of a decreasing quantity of the $CO_2$ and the EtOH vapor produced during the yeast-based metabolic processing cycle, and recovering the alcoholic liquid condensate in a condensate recovery vessel.

2. The process of claim 1, wherein the starting material is selected from the group consisting of grapes, plums, cherries, peaches, apples, berries, rice, corn, potato, sugar cane juice.

3. A process for co-production of wine or wine-precursor during a yeast-based metabolic processing cycle from a starting material including a liquid derived from grapes and non-liquid grape solids contained within a batch-type fermentation vessel and a distilled alcoholic spirit from EtOH vapors present in the headspace of the fermentation vessel in which quantities of $CO_2$ and EtOH vapor are produced therein during the yeast-based metabolic processing cycle, any variations in pressure within the headspace of the fermentation vessel substantially related to variations in the quantities of the $CO_2$ and the EtOH vapor produced therein during the yeast-based metabolic processing cycle, comprising the steps of:

connecting a flow pathway between the headspace of the fermentation vessel and a variable-capacity condensation device for flowing at least a portion of the $CO_2$ and the EtOH vapor from the headspace therethrough and into the condensation device, the condensation device having a condensing capacity sufficient to condense at least 35% of the EtOH vapor passing therethrough into a liquid, the flow rate of the CO2 and the EtOH vapor from the headspace of the fermentation vessel through the vapor flow pathway being at least responsive to the quantity of the CO2 produced during the yeast-based metabolic processing cycle in the fermentation vessel, the aggregate flow restriction of the flow path and the condensation device insufficient to cause no more than an about a 0.50 psi rise in the pressure within the fermentation vessel, the variable-capacity condensation device controlled by a stored-program controlled processor in response a sensor responsive to the flow rate in the flow pathway, supplying heat sufficient to raise the temperature of the major portion of the surfaces of the flow pathway in contact with the $CO_2$ and the EtOH vapor flowing therethrough to a temperature at least four to six degrees F. greater than the temperature of the flow therein; condensing at least a portion the EtOH vapor into a liquid alcoholic spirit, increasing the condensing capacity of the condensation device in incremental steps as a function of an increasing quantity of the $CO_2$ and the EtOH vapor produced during the yeast-based metabolic process, and decreasing the condensing capacity of the condensation device in decremental steps as a function of a decreasing quantity of the $CO_2$ and the EtOH vapor produced during the yeast-based metabolic process, recovering the condensed EtOH vapor as a distilled alcoholic spirit, and recovering the liquid wine or wine-precursor product from the fermentation vessel.

* * * * *